United States Patent [19]
Walton

[11] Patent Number: 5,497,099
[45] Date of Patent: Mar. 5, 1996

[54] ANTENNA SYSTEM FOR SOOT DETECTING

[75] Inventor: Frank B. Walton, Pinawa, Canada

[73] Assignee: Engine Control Systems Ltd., Canada

[21] Appl. No.: 204,255

[22] PCT Filed: Sep. 3, 1992

[86] PCT No.: PCT/CA92/00374

§ 371 Date: Mar. 4, 1994

§ 102(e) Date: Mar. 4, 1994

[87] PCT Pub. No.: WO93/05388

PCT Pub. Date: Mar. 18, 1993

[30] Foreign Application Priority Data

Sep. 6, 1991 [JP] Japan .................. 3-227355

[51] Int. Cl.$^6$ .................................................. G01R 27/32
[52] U.S. Cl. ........................................ 324/641; 324/639
[58] Field of Search .................... 324/452, 637, 324/639, 641, 647, 659, 663, 672

[56]  References Cited

U.S. PATENT DOCUMENTS

| | | | |
|---|---|---|---|
| 3,104,354 | 9/1963 | Weinschel et al. | 324/58 |
| 3,277,366 | 10/1966 | Webb | 324/57 |
| 3,526,834 | 9/1970 | Brown | 324/57 |
| 3,758,851 | 9/1973 | Yokoyama et al. | 324/659 |
| 4,042,879 | 8/1977 | Ho et al. | 324/636 |
| 4,077,003 | 2/1978 | Rau | 324/338 |
| 4,135,131 | 1/1979 | Larsen et al. | 324/639 |
| 4,477,771 | 10/1984 | Nagy et al. | 324/636 |
| 4,503,384 | 3/1985 | Nagy et al. | 324/690 |
| 4,507,602 | 3/1985 | Aguirre | 324/638 |
| 4,580,441 | 4/1986 | Sakurai et al. | 73/28 |
| 4,710,757 | 12/1987 | Haase | 324/663 X |
| 4,764,718 | 8/1988 | Revus et al. | 324/640 |
| 4,943,778 | 7/1990 | Osaki | 324/636 |
| 4,947,129 | 8/1990 | Helms et al. | 324/640 |
| 5,157,340 | 10/1992 | Welton et al. | 324/641 |
| 5,177,444 | 1/1993 | Cutmore | 324/637 |
| 5,223,782 | 6/1993 | Dutta et al. | 324/452 X |
| 5,369,369 | 11/1994 | Cutmore | 324/637 |

FOREIGN PATENT DOCUMENTS

WO-A-9202807  2/1992  WIPO.

Primary Examiner—Kenneth A. Wieder
Assistant Examiner—Glenn W. Brown
Attorney, Agent, or Firm—Hayes, Soloway, Hennessey, Grossman & Hage

[57]  ABSTRACT

An apparatus for detecting the accumulation of particulate material on a filter medium formed of dielectric material and disposed in a chamber is provided. The apparatus is operable for generating and transmitting an RF signal through the filter medium and for monitoring the transmission loss of the signal through at least a portion of the filter medium so as to provide an indication of the content of particulate material accumulated on the filter medium. The apparatus includes an input antenna for transmitting the signal and having at least one antenna element extending longitudinally of the chamber and disposed within the filter medium; and an output antenna for receiving the signal transmitted by the input antenna and having at least one antenna element extending longitudinally of the chamber and disposed within the medium in parallel, spaced apart, axially overlapping relation with respect to the input antenna element.

7 Claims, 8 Drawing Sheets

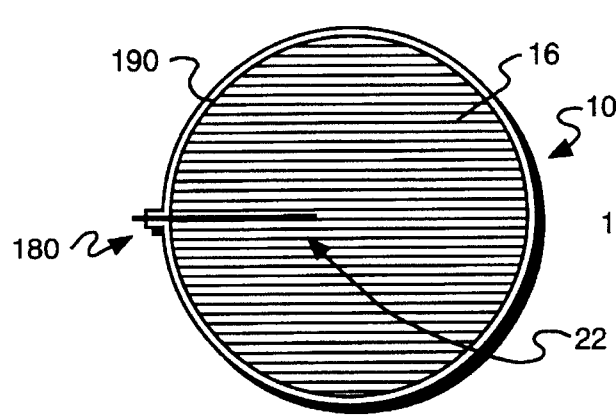 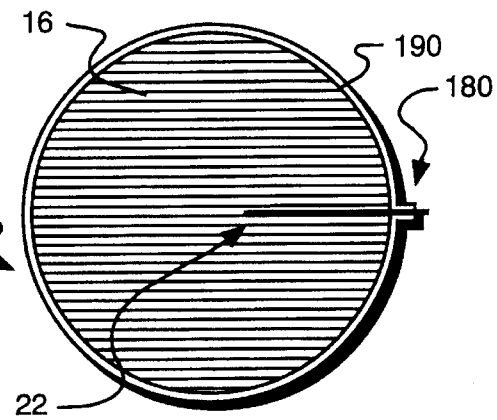
FIG. 3a            FIG. 3b
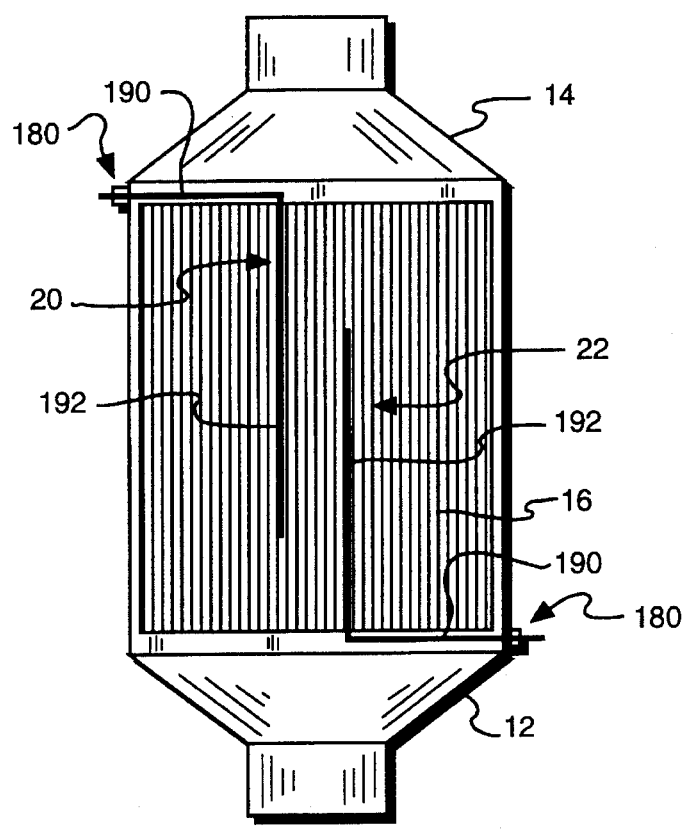
FIG. 3c

ANTENNA SYSTEM FOR SOOT DETECTING

The present invention relates, in general, to an apparatus for detecting the concentration or level of accumulation of RF susceptible, particulate material on a filter medium and, more specifically, to an antenna system for use therein.

BACKGROUND OF THE INVENTION

As is well known, a filter is placed in the exhaust system of diesel engines to remove soot from the exhaust gases of the engine. The filter must be changed or cleaned from time to time to ensure that soot accumulations do not adversely affect engine operation. It is known to remove or incinerate the soot particles by subjecting the filter, in situ, to heat from a fuel burner or other heat generating device, or from suitable running of the engine. Incineration is to be performed when the accumulation has reached a level where further accumulation would adversely affect engine performance or before that incineration would produce excessive temperatures and possibly damage the filter. There is a need, therefore, for a method and apparatus which monitors the level of soot accumulation and provides a signal when the accumulation reaches a predetermined level.

Soot accumulations exhibit dielectric properties. Accordingly, it is possible to monitor the level of soot accumulation on a diesel engine filter medium by detecting changes in the effective dielectric properties of the filter medium. The complex permittivity of a material is comprised of two components: a real component called the "dielectric constant" and an imaginary component called the "dielectric loss factor". Changes in either of these components can be detected using RF interrogation methods. It should be mentioned at this point that the dielectric constant and loss factor of soot increases with increasing temperature. This affects both transmission and reflection (resonance) type of measurements.

One method of applying this concept to monitoring soot levels in diesel filters is to construct the filter housing or containment in the form of a RF waveguide and then periodically excite the waveguide with RF energy at a fixed frequency and measure the reflected power. The reflected power will be a function of soot accumulation on the filter. More specifically, for any RF system, it is usually possible to determine a frequency at which the electrical load, i.e. the filter medium, the diesel soot and the filter containment, represents a matched impedance with respect to the power source. In other words, the equivalent electrical resistance, capacitance and/or inductance of the load are matched to the RF power source. When the load impedance is perfectly matched to the power source, all emitted RF power is absorbed by the load. If the impedance is not matched to the RF source, some of the RF power will be reflected from the load. The degree of load mismatch determines the mount of reflected power and, hence, reflected power can be used to measure the change in the effective dielectric constant. This method can be generally referred to as a reflectance or resonance type of measurement.

U. S. Pat. No. 4,477,771 granted to the General Motors Corporation on Oct. 16, 1984 describes a method of detecting soot content in a particulate trap using this method. The method detects changes in the effective dielectric constant only. The patent provides a metal filter housing constructed as cylindrical waveguide which defines a closed, RF resonance cavity for receiving a ceramic filter. A single probe is positioned at one end of the cavity and behaves as both a transmitting and a receiving antenna. A reflective screen is positioned at the opposite end of the cavity. All connecting exhaust pipe diameters are below the cutoff diameter of a circular waveguide needed to transmit the RF energy at the frequencies used in the device. The probe is connected to a RF source through a directional coupler and an isolator. A detector is also connected to the probe through the directional coupler. In one mode of operation of the device, the RF source is operated at the resonant frequency of the cavity when the filter is loaded with particulates to its maximum desired accumulation and the detector is operated to detect a null condition in the reflected signal which occurs at the resonant condition. Upon detecting such a condition, the detector generates an output signal operable to effect operation of a lamp or alarm. In a second embodiment, the reflective screen is replaced by a second probe positioned at the remote end of the cavity. One probe is connected to the power source and the other probe is connected to the detector.

There are a number of practical and technical problems with this approach. From a practical point of view, it is important to understand that the commercial viability of a RF-based device depends on its component count and, more on its component price. In this latter respect, higher operating frequencies incur higher component and fabrication costs. The device also tends to display poor sensitivity and is prone to large measurement errors due to the effect of temperature on the effective dielectric constant for reasons described below.

From a technical point of view, there are two factors which must be considered and which have been overlooked by the prior art. One factor relates to the properties of the filter containment or housing and the other relates to the properties of soot. Dealing firstly with the filter housing, based on wavelength considerations, there is a frequency below which a waveguide will not allow RF energy to propagate without significant attenuation. The frequency below which this occurs is called the "cutoff frequency" for that waveguide geometry. The formula for calculating this cutoff frequency and the attenuation for the transmission of frequencies below cutoff is well known to those knowledgeable in the art. It can be shown, for example, that the cutoff frequency for a 14.4 cm diameter filter is greater than 1.2 GHz and for a 30.5 cm diameter filter, the cutoff frequency is greater than 0.5 GHz. If the filter containment is a cylindrical resonator and the frequency for the lowest mode (and frequency) for resonance is calculated, one finds that for the smaller filter (14.4 cm Diameter×15.24 cm Long) the $TE_{111}$ resonant frequency is 1.6 GHz and for a $TM_{111}$ resonance, the resonant frequency is 1.9 GHz. Similarly, for a 28.6 cm Diameter×30.48 cm long filter, the $TE_{111}$ resonant frequency is 0.79 GHz and, for the $TM_{111}$ mode, the frequency is 0.94 GHz. These calculations clearly indicate that conditions for resonance require even higher frequencies than for transmission. These high frequencies result in high component and fabrication costs.

The properties of soot (carbon particulates) also have a significant impact on viability of RF-based measurement methods. Soot is a particularly lossy dielectric and it is for this reason that carbon black (soot) is added to materials like rubber to increase the carrier's ability to be heated in a RF field. Terminal loads for RF systems are also constructed of carbon. The dielectric constant of the soot changes with temperature and hence the effective dielectric constant of the filter changes with temperature. This means that the resonant frequency shifts with changes in both soot accumulation and temperature. Clearly, this effect must be accounted for in measuring soot accumulation in a filter heated by hot diesel exhaust. This factor adds to the complexity and cost of the device.

For either of the methods proposed in the above described patent, the metal housing containing the empty filter must act as a narrow bandpass RF filter in order to make the measurements described in the patent. That is to say, the resonant cavity thus formed should allow energy to enter the cavity over only a very narrow range on either side of the resonant frequency and reject or reflect RF energy at all other frequencies (i.e., a narrow bandpass RF filter). Unfortunately for the methods described in the patent, the accumulation of soot not only changes the effective dielectric constant of the filter, thereby shifting the resonant frequency of the cavity, but it is also causes the cavity to increase its bandpass frequency range due to the effects of the very high dielectric loss factor of the soot, a factor not considered in the patent. In fact, above a range of soot load and temperature combination, the soot becomes a purely resistive load over a wide range of frequencies (i.e., it becomes a broadband terminal carbon load). When the load becomes mainly resistive in nature, reflections drops virtually to zero. Since this phenomenon is broadband in nature, it is no longer possible to measure a resonant frequency (i.e., there is no difference in the amount of power being reflected over a wide range of frequencies).

In summary, reflectance or resonance type measurements of the type described in the above mentioned patent arc precluded from using frequencies below the resonant frequency defined by the geometry of each filter and/or its metal containment. There is a manufacturing cost penalty associated with the relatively high frequencies that must be used by these methods. The high loss factor of the soot, as determined by soot concentration, temperature and RF frequency, places severe restrictions on the range of soot concentration that can be measured. In short, these methods are not commercially viable.

SUMMARY OF THE INVENTION

The present invention seeks to provide a soot monitoring device which controls signal attenuation to levels which can be measured by conventional and relatively inexpensive electronic systems. To meet this objective, the present invention provides an antenna system which does two things. First, it restricts the transmission loss measurement to only a fraction of the filter volume, thereby reducing the amount of soot in the RF signal path, and, second, the geometry of the antenna system is arranged such that it does not require the filter housing to serve as a waveguide, thereby eliminating a number of the technical problems mentioned earlier and, thus, allowing the device to be used at frequencies in the low MHz range. The lower frequencies mean lower signal attenuation and lower device costs.

In its most basic form, the antenna system consists of parallel transmitting and receiving antennae that are inserted parallel to the central axis of the cylindrical metal filter cavity and are inductively coupled in a direction radial to the antennae and filter axis. These antennae may be inserted in either end of the filter or both in the same end of the filter. It can be readily demonstrated that the measurement volume is axially confined to the area of overlap of the antennae and in the radial direction by the metal walls of the filter housing. Each antenna may consist of one or more metallic elements. The addition of more than one element to an antenna may be desirable in some applications in order to improve the broadband frequency transmission and reception characteristics of the antenna system. The antenna system design geometry is closely coupled to the geometry of the filter. That is, the antenna geometry is adjusted to optimize transmission and reception of a selected frequency range within a specific filter system geometry.

The present invention is generally defined as an improved antenna system for an apparatus for detecting the accumulation of particulate material on a filter medium formed of dielectric material and disposed in a chamber, the apparatus being operable for generating and transmitting a RF signal through the filter medium and for monitoring the transmission loss of the signal through at least a portion the filter medium so as to provide an indication of the content of particulate material accumulated on the filter medium, the improvement comprising an input antenna for transmitting the signal and having at least one antenna element extending longitudinally of the chamber and disposed within the filter medium; and an output antenna for receiving the signal transmitted by the input antenna and having at least one antenna element extending longitudinally of the chamber and disposed within the medium in parallel, spaced apart, axially overlapping relation with respect to the input antenna element.

BRIEF DESCRIPTION OF THE DRAWINGS

These and other features of the invention will become more apparent from the following description in which reference is made to the appended drawings wherein:

FIGS. 3a, 3b and 3c are top, bottom and side cross-sectional views of one embodiment of the antenna system of the present invention in which the antenna system is characterized by a pair of inductively coupled monopole antennae inserted into the exhaust inlet and outlet ends of a wall-flow filter within a metal filter housing;

DESCRIPTION OF PREFERRED EMBODIMENT

Figure 1:
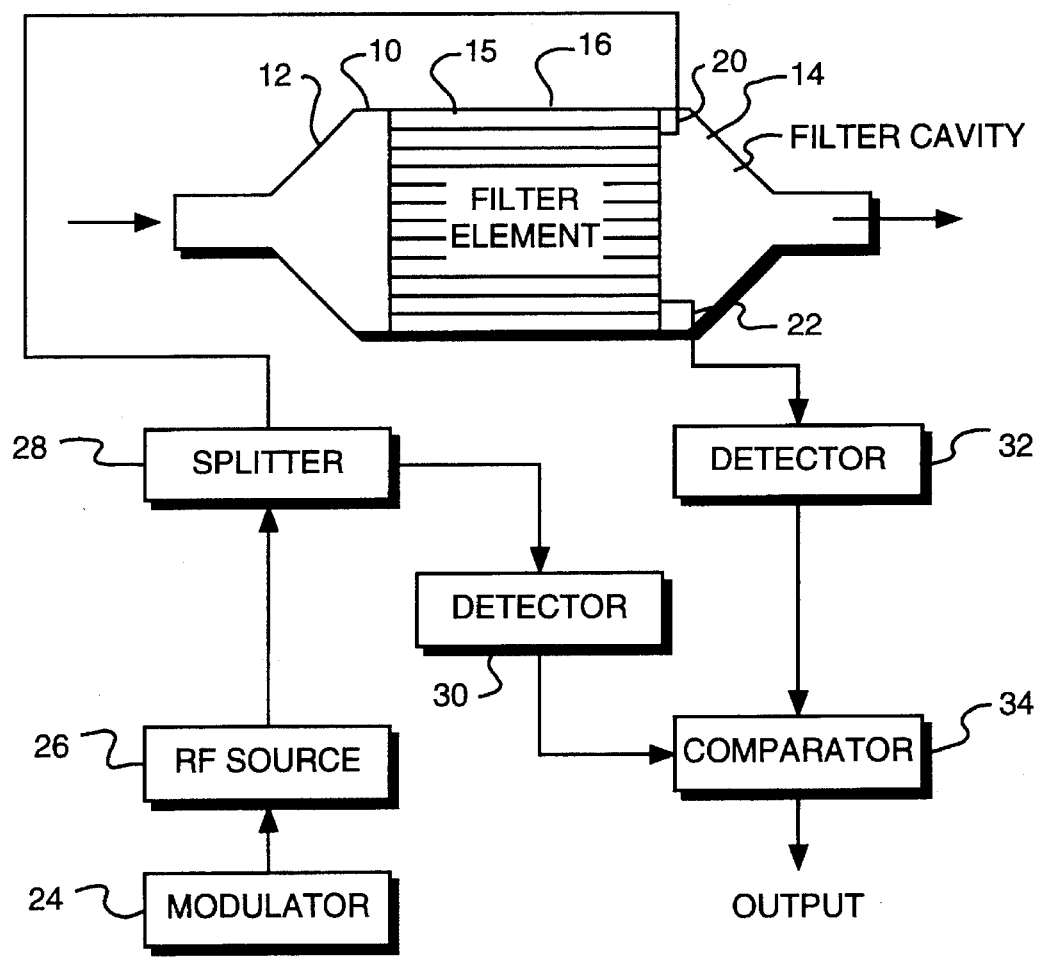
FIG. 1 is a diagrammatic, gross-sectional view of a diesel exhaust particulate trap or filter adapted for RF detection of the soot accumulation and a block diagram of an electrical circuit for carrying out the method of the present invention.

FIG. 1 illustrates a steel, cylindrical filter housing 10 having frusto-conical steel inlet and outlet end sections 12 and 14 adapted to be connected to engine exhaust pipes in a manner well known in the art. The housing is formed with a chamber 15 to receive a ceramic filter element 16 of suitable construction. A first probe 20 which behaves as a transmitting antenna for RF power and a second probe 22 which behaves as a receiving antenna for RF power are disposed within the housing and embedded within the filter element in a manner which is explained more fully below. A modulator 24 generates an amplitude modulated tone signal which is fed to an RF source 26 which, in turn, generates a carrier signal for the tone signal and applies the resulting signal to a splitter 28. Splitter 28 applies the signal to both transmitting probe 20 and a first detector 30. Detector 30 produces a reference output signal which is representative of the power of the signal prior to transmission. The use of an amplitude modulated signal allows the signal to be much more easily detected than by the method used in the aforementioned General Motors Corporation patent.

A second detector 32, electrically connected to the second probe, produces an output signal representative of the power of the signal received by the second probe 22. The first and second detector output signals are applied to a comparator 34 which produces an output signal which is proportional to the difference in the signal strength of the transmitted and received signals. Accordingly, the comparator output signal is representative of the transmission loss through the filter medium which, in turn, is representative of the change in the effective dielectric loss factor caused by accumulation of soot on the filter. It will be seen therefore that when there is little or no accumulation in the filter, there will be only a small transmission loss in the signal strength. As the soot accumulation increases, the difference in signal strength between the transmitted and received signals changes, resulting eventually in an output signal from the comparator. The comparator can be designed to drive a variable output display or an indication when a predetermined level is reached, or both.

The power source is arranged to emit RF energy over a range of frequencies with the preferred frequency band being up to one octave, i.e. a 2 to 1 range, in frequency. An appropriate frequency band is 150 MHz to 250 MHz. There are three reasons for this. First, the average transmission loss through the filter over the selected frequency range results in better measurement sensitivity, i.e. attenuation per unit of soot present, and a more linear response as a function of RF signal attenuation than is possible at a single frequency. Second, it avoids problems associated with power source frequency drift with time. Third, the use of an averaging process demonstrably reduces the effects of temperature on transmission losses, i.e. the effects of temperature on soot and filter permittivity, which would otherwise require temperature compensation in single or narrow band frequency methods.

Figure 2:
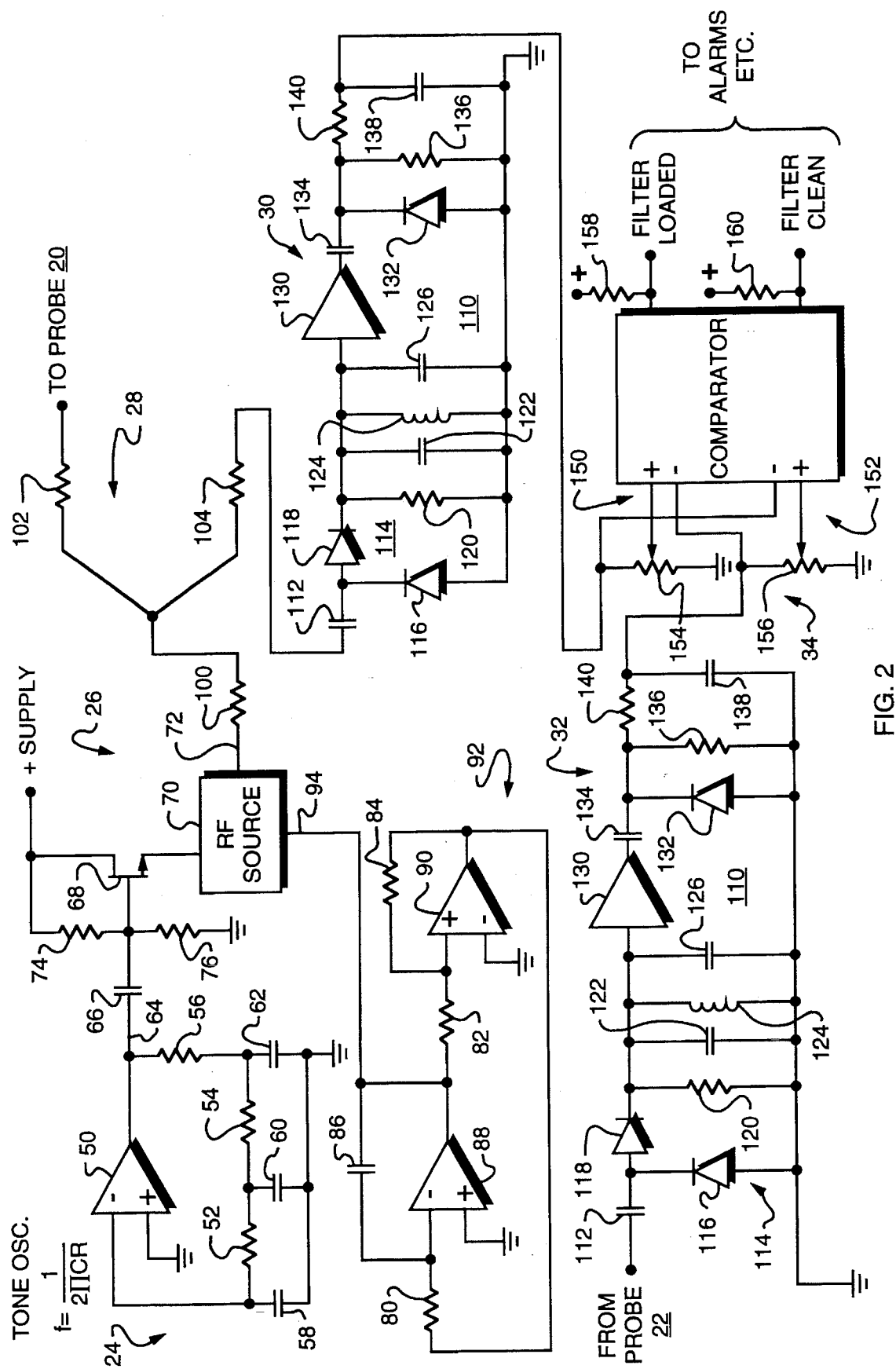
FIG. 2 is a schematic of an electrical circuit in accordance with an embodiment of the present invention.

With reference to the circuit diagram illustrated in FIG. 2, modulator 24 will be seen to be comprised of an operational amplifier 50 which, with resistors 52, 54 and 56 and capacitors 58, 60 and 62, forms a phase shift audio oscillator which provides a tone modulated signal along line 64. This signal is fed via capacitor 66 to the gate of a FET modulator transistor 68 which directly modulates the power supply to a frequency swept RF source 70, thereby imposing an AM audio tone on the RF signal output along line 72. Resistors 74 and 76 form the gate bias network for transistor 68. Resistors 80, 81 and 84, capacitor 86 and operational amplifiers 88 and 90 form a sawtooth waveform sweep generator 91 which feeds a swept output signal to the frequency control port 94 of the RF source so as to cause the RF oscillator output to vary by up to one octave in frequency. The sweep rate is set by resistor 80 and capacitor 86. The output of the RF source is applied to splitter 18 which is simply comprised of a resistor 100 in series with resistors 101 and 104, respectively. The output of resistor 102 is fed to the transmit antenna or probe 20 while the output of resistor 104 is fed to the input of reference detector 30. For equal power division, the resistances of the three resistors are equal. The values of the resistances may be varied so that match is preserved with the system impedance but with most of the power passed to the soot filter.

Reference detector 30 and the signal detector 32 may be of identical construction as indicated by subcircuits 110 in FIG. 2. Each circuit 110 includes a capacitor 112 which provides DC isolation from a low-resistance source for a voltage-doubler signal detector 114 comprised of diodes 116 and 118. Resistors 120 and Capacitor 122 provide a level enhancing time constant for the detected modulation tone. Inductor 124 and capacitor 126 form a parallel tuned circuit at the tone frequency which curtails the passband and improves the signal to noise ratio. Capacitor 128 prevents inductor 124 from shorting resistor 120. Operational amplifier 130 amplifies the signal tone by about 30 dB. Diode 132 rectifies the amplified tone signal to DC, with capacitor 134 and resistor 136 setting the time constant and capacitor 138 and resistor 140 serving as a ripple filter. Each of the two detectors feed a respective input to the comparator.

Comparator 34 is formed with two sections generally designated by reference numerals 150 and 152. The reference detector output is fed directly to the negative input of the second section 152 and indirectly to the positive input of the first section 150 through a potentiometer 154. Similarly, the signal detector output is fed directly to the negative input of the first section 150 and indirectly to the positive input of the second section 152 through a potentiometer 156. The potentiometers serve to set the input levels from the signal and reference detectors to the two sections of the comparator. More specifically, in one section, potentiometer 154 sets its input below the output signal of the signal detector. As the signal level declines with increasing soot, a point is reached where the negative input to this section drops below the positive input and the output of the section is then pulled up by resistor 158. In the other section, potentiometer 156 is set so that the positive input is above the reference detector output only when the soot filter is clean. This serves as an optional check on the burn-clean cycle. With the signal above the reference detector, resistor 160 pulls up this output. The outputs are connected to indicator circuits not shown.

Figure 4A:
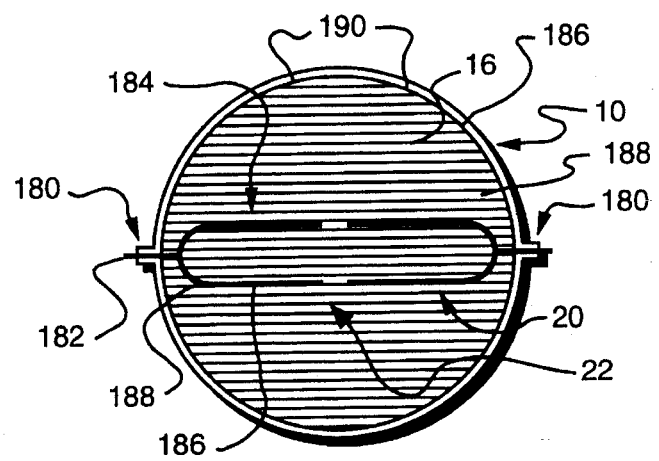
FIGS. 4a, 4b and 4c are top and side cross-sectional views of a second embodiment of the antenna system of the present invention in which the antenna system is characterized by a pair of inductively coupled bipolar antennae are both inserted into either the exhaust inlet or exhaust outlet end of a wall-flow filter within a metal filter housing.
Figures 4B, 4C:
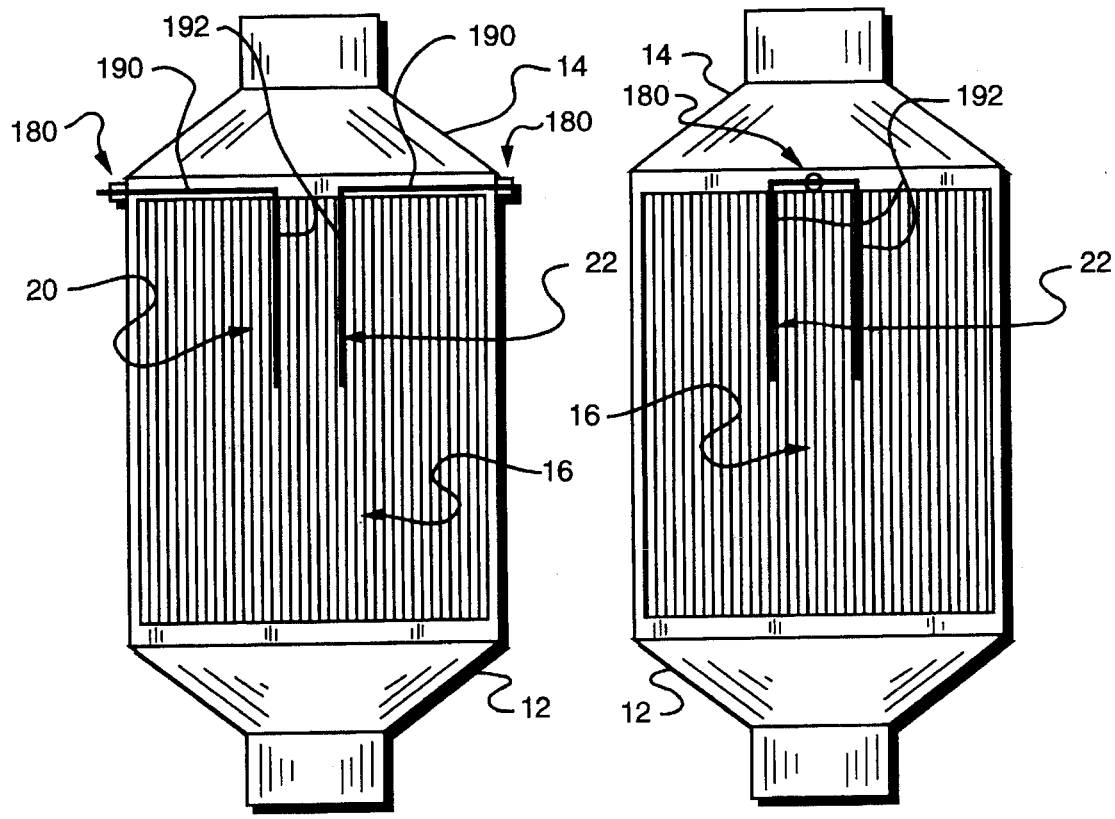
Figure 5:
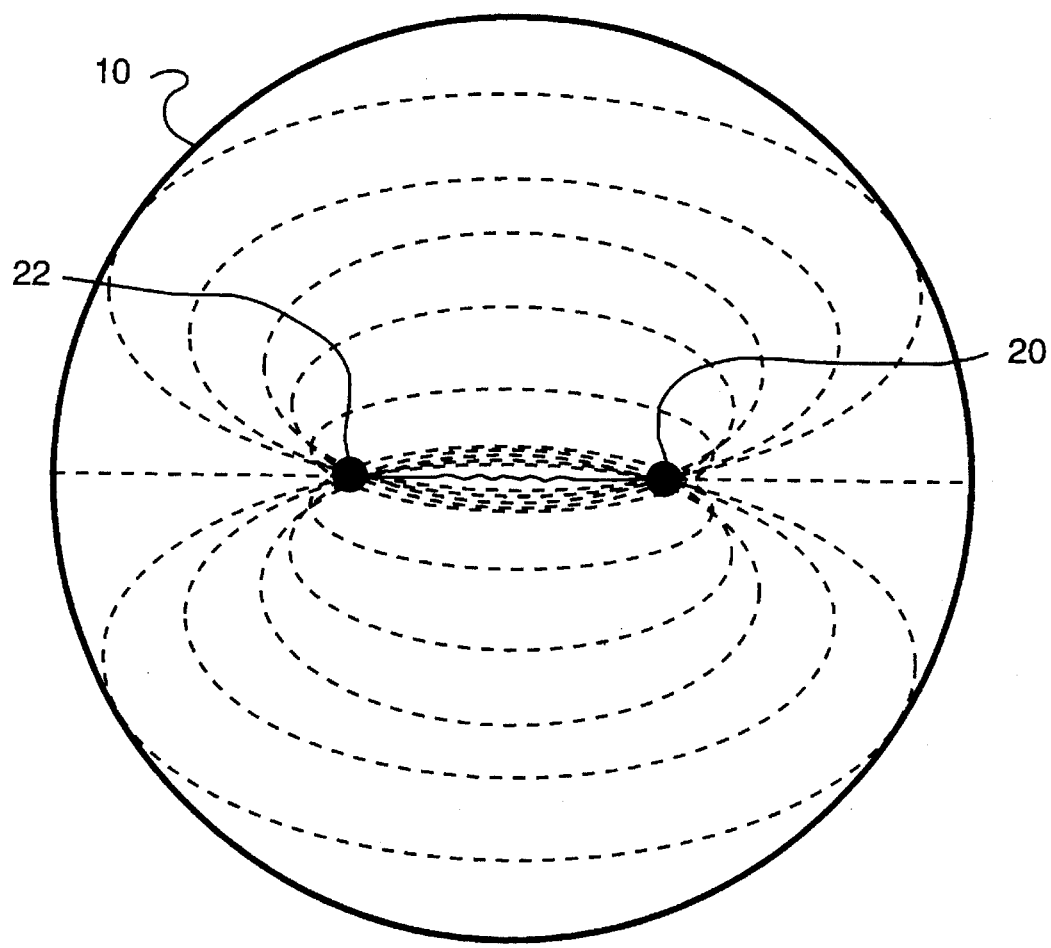
FIG. 5 is a diagrammatic gross-sectional view illustrating the electric field pattern within a filter cavity for a pair of inductively coupled monopole antennae.

FIGS. 3–5 illustrate two embodiments of an antenna system for use in a wall-flow filter system, although it is to be understood that the antenna system be used with other filter types, such as ceramic foam filters and the like, and/or other geometries, without departing from the spirit of the invention. The antenna system has been designed to provide a soot monitoring device which reduces signal attenuation to levels which can be measured by conventional and relatively inexpensive electronic systems. To that end, the antenna system does two things. First, it restricts the transmission loss measurement to only a fraction of the filter volume, thereby reducing the mount of soot in the RF signal path. In the aforementioned United States patent, the RF signal must propagate through the entire axial length of the filter. This requires more power, more complex circuitry and more expense. Second, the geometry of the antenna system is arranged such that it does not require the filter housing to serve as a waveguide. This eliminates a number of the technical problems mentioned earlier, particularly those associated with the cutoff frequency. Thus, the device can be used at frequencies in the low MHz range, well below the cutoff frequency of the same housing used as a waveguide. The lower frequencies mean lower signal attenuation and lower device costs.

In its most basic form, the antenna system consists of parallel transmitting and receiving antennae that are inserted into the filter medium, parallel to the central axis of housing. The antennae may be inserted into either end of the filter or both in the same end of the filter. The antennae are inductively coupled in a radial direction with respect to the antennae and the filter axis. It can be readily demonstrated that the measurement volume is axially confined to the area of overlap of the antennae and radially confined by the metal walls of the filter housing. Each antenna may consist of one or more metallic elements. The addition of more than one element to an antenna may be desirable in some applications in order to improve the broadband frequency transmission and reception characteristics of the antenna system. The antenna system design geometry is closely coupled to the geometry of the filter. That is, the antenna geometry is adjusted to optimize transmission and reception of a selected frequency range within a specific filter system geometry.

Figures 6, 7:
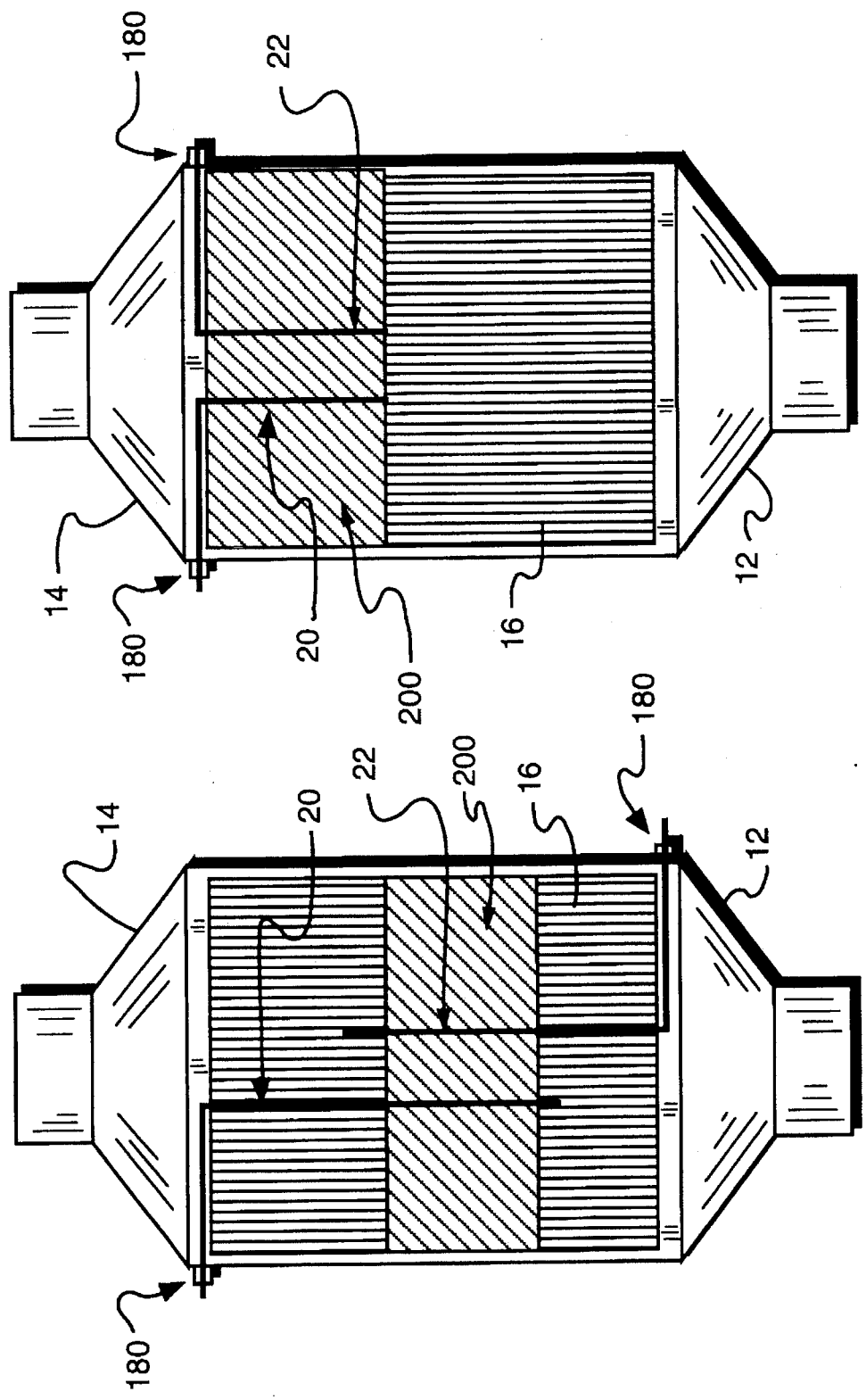
FIGS. 6 and 7 are schematic representations of the RF-measurement volume associated with the region of antennae axial overlap for two types of antennae insertion methods.

In the embodiment of FIG. 3, the antenna system is comprised of a pair of inductively coupled monopole antennae inserted into opposite ends of a wall-flow filter disposed within a metal filter housing. The two elements are parallel to one another and the axis of the filter element but axially overlap one another, as best shown in FIG. 6, to define an RF-Measurement volume 200. In the embodiment of FIG. 4, the antenna system is comprised of a pair of inductively coupled bipolar antennae inserted into the same end, either the inlet or the outlet end, of a wall-flow filter disposed within a metal filter housing. The two elements are parallel to one another and the axis of the filter element and axially overlap one another, as best shown in FIG. 7, to define an RF-Measurement volume 200.

The antenna elements of the two illustrated embodiments are secured to the RF feed-through-fittings and embedded in the filter element in the same manner, as described hereinafter. Transmitting antenna 20 and a receiving antenna 22 extend through the wall of the vessel, through the RF feed-through-fittings 180, and penetrate the filter medium. Each antenna includes a straight conductor portion 182 which passes through its associated fitting and a pair of laterally spaced arms 184 and 186 connected together by a semi-circular portion 188. Each arm is generally L-shaped with a radial or transverse portion 190 and an axial portion 192. As shown in the drawings, the axial portion penetrates the filter medium. For illustration purposes, for a filter containment vessel with a length and diameter of 30.5 cm, the lateral spacing between antenna arms may be 40 mm, the radial portion of the arms may be 90 mm, the axial length of arm penetration into filter may be 120 mm, the offset of the semi-circular portion from filter containment wall may be 20 mm and the radius of curvature of semi-circular portion may be 20 mm. It will be obvious to those skilled in the art that there are variations on the above which might be better or equally good insofar as antenna performance is concerned. It will also be understood that while two arms have been shown, improved performance might be achieved by the addition of a third arm to the antenna.

By adding to the number and/or modifying the position and/or length of the various metallic antenna elements, it should be understood that both the size and/or the shape of the filter volume sampled by the antenna system may be modified to suit various measurement requirements.

Figure 8:
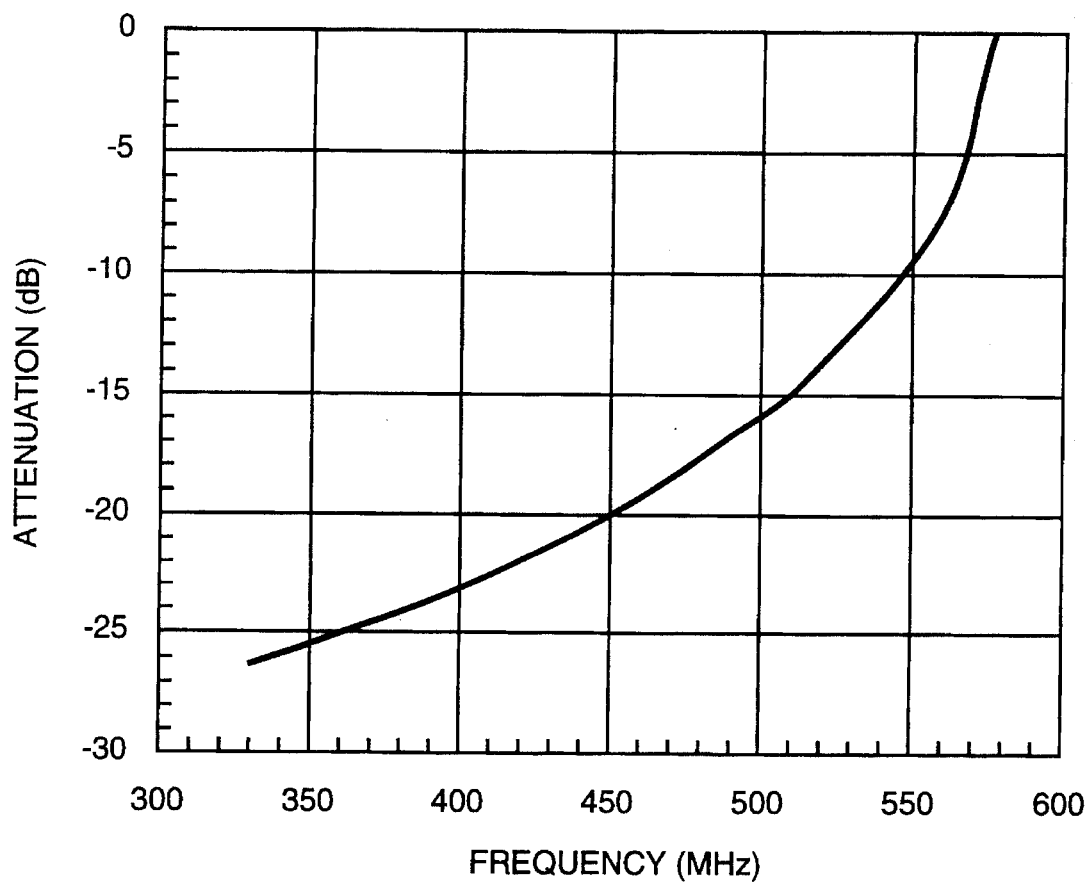
FIG. 8 is a graph illustrating TEM mode transmission loss as a function of frequency for a 30.48 cm long cylindrical waveguide.

FIG. 8 plots the attenuation through the length of the filter containment for a 30.5 cm D×30.5 cm L filter. The actual path length is longer for an antenna at each length because it is not always possible to place the antenna at the filter face and, hence, the actual transmission losses shown in FIG. 8 are conservative. The graph ignores other losses in the filter (i.e., filter and/or soot).

Figure 9:
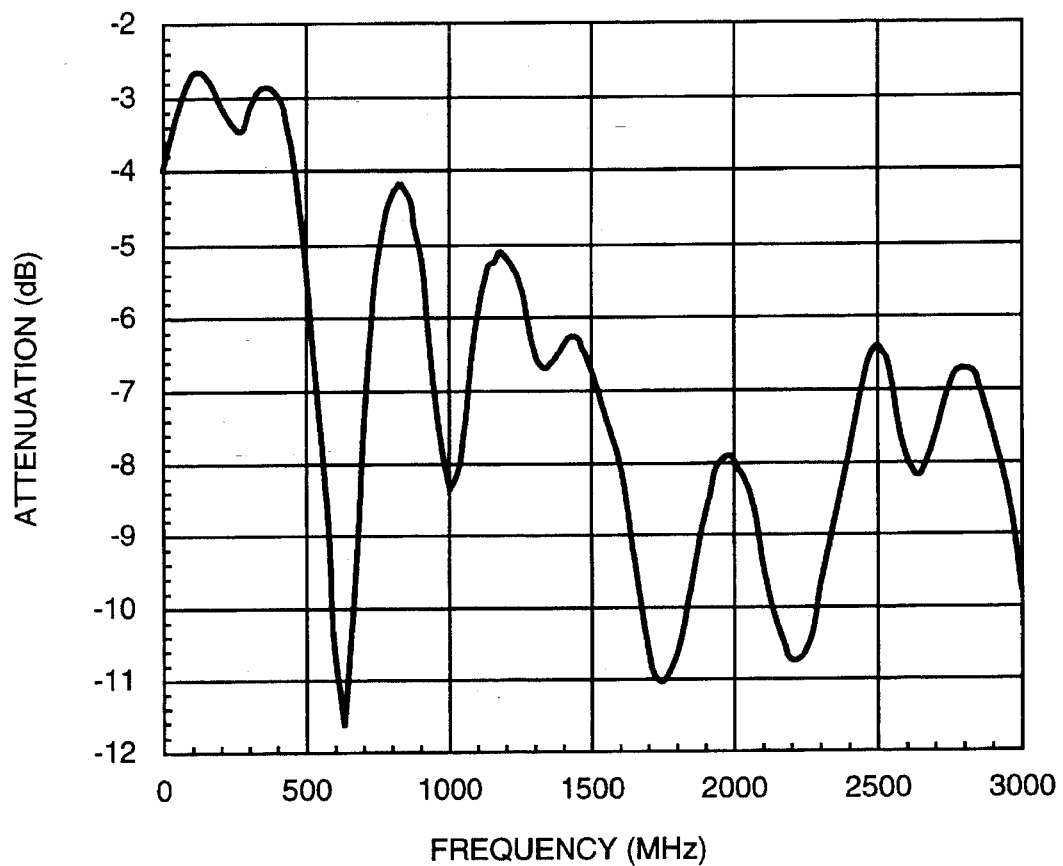
FIG. 9 is a graph illustrating RF transmission loss as a function of frequency.

If it was desired to use an RF source in the 200 to 300 MHz range with conventional antenna methods, i.e., end-to-end transmission, in a 30.5 cm diameter by 30.5 cm long wall-flow filter system, the total transmission loss would be estimated as follows. The (measured) transmission loss of a filter loaded to approximately 5 g/L is about 30 dB. From FIG. 8, the transmission loss due to frequency cutoff at 300 MHz is about 30 dB. Thus, the total transmission loss of a loaded filter is 30+30=60 dB. This mount of transmission loss is clearly outside the range, normally 20 to 30 dB, of a practical industrial device. FIG. 9 shows the transmission loss as a function of frequency for a comparable system constructed according to the present invention. Losses in the range of 200 to 300 MHz are around 3 dB—an order of magnitude improvement over convention antenna methods.

It will be understood that various modifications and alterations may be made to the present invention without departing from the spirit of the appended claims.

The embodiments of the invention in which an exclusive property of privilege is claimed are defined as follows:
PROPERTY OF PRIVILEGE IS CLAIMED ARE DEFINED AS FOLLOWS:

1. In an apparatus for detecting the accumulation of particulate material on a filter medium, the filter medium formed of dielectric material and disposed in a chamber, said apparatus having means for generating and transmitting an RF signal through said filter medium and for monitoring the transmission loss of said signal through at least a portion of said filter medium so as to provide an indication of the content of particulate material accumulated on said filter medium, the improvement comprising:

an input antenna for transmitting said signal and having at least a first antenna element extending longitudinally within said chamber and disposed within said filter medium; and an output antenna for receiving the signal transmitted by said input antenna and having at least a second antenna element extending longitudinally within said chamber and disposed within said medium in parallel, spaced apart, axially overlapping relation with respect to said first antenna element.

2. The apparatus as defined in claim 1, wherein said input antenna and output antenna are inserted into opposite ends of said filter medium.

3. The apparatus as defined in claim 1, wherein said input antenna and said output antenna are inserted into the same end of said filter medium.

4. The apparatus as defined in claim 1, wherein said first antenna element having a first arm portion laterally spaced from a second arm portion of the second antenna element and a first connecting portion at an end of said first arm portion for connecting with a second connecting portion of the second antenna element.

5. The apparatus as defined in claim 4, wherein each of said input antenna and output antenna has a conductor portion which passes through a wall of said chamber, and one end of said conductor portion is connected to a connecting portion of each said antenna element within said chamber.

6. The apparatus as defined in claim 1, wherein said input antenna transmits said RF signal at frequencies in the lower MHz range than the cutoff frequency of said chamber.

7. The apparatus as defined in claim 6, wherein said input antenna transmits said RF signal at frequencies in the range of 150–250 MHz.

* * * * *